(12) United States Patent
Griswold et al.

(10) Patent No.: US 11,372,069 B2
(45) Date of Patent: Jun. 28, 2022

(54) SYSTEM AND METHOD FOR DEPLOYING INTERVENTIONAL MEDICAL DEVICES USING MAGNETIC RESONANCE FINGERPRINTING (MRF)

(71) Applicant: Case Western Reserve University, Cleveland, OH (US)

(72) Inventors: Mark A. Griswold, Cleveland, OH (US); Cameron McIntyre, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 428 days.

(21) Appl. No.: 16/686,828

(22) Filed: Nov. 18, 2019

(65) Prior Publication Data
US 2020/0158805 A1  May 21, 2020

Related U.S. Application Data

(60) Provisional application No. 62/768,177, filed on Nov. 16, 2018.

(51) Int. Cl.
| | | |
|---|---|---|
| *G06K 9/00* | (2022.01) | |
| *G01R 33/56* | (2006.01) | |
| *G01R 33/48* | (2006.01) | |
| *G01R 33/50* | (2006.01) | |

(52) U.S. Cl.
CPC ..... *G01R 33/5608* (2013.01); *G01R 33/4806* (2013.01); *G01R 33/50* (2013.01); *G06T 2207/10088* (2013.01); *G06T 2207/20084* (2013.01); *G06T 2207/20112* (2013.01); *G06T 2207/30016* (2013.01)

(58) Field of Classification Search
CPC ........... G01R 33/5608; G01R 33/4806; G01R 33/50; G06T 2207/10088; G06T 2207/20084; G06T 2207/20112; G06T 2207/30016
USPC ....................................................... 382/128
See application file for complete search history.

(56) References Cited

U.S. PATENT DOCUMENTS

| | | | |
|---|---|---|---|
| 8,723,518 B2 | 5/2014 | Seiberlich | |
| 2015/0301141 A1 | 10/2015 | Griswold | |
| 2017/0146623 A1* | 5/2017 | Cohen | ............... G01R 33/5602 |

OTHER PUBLICATIONS

Magnetic Resonance Fingerprinting for Target Identification in Deep Brain Stimulation, Jun. 2018, ASSFN 2018 Biennial Meeting, pp. 1-2 (Year: 2018).*

(Continued)

*Primary Examiner* — Jonathan S Lee
(74) *Attorney, Agent, or Firm* — Quarles & Brady LLP

(57) ABSTRACT

A method for target identification for a deep brain stimulation procedure includes acquiring a set of magnetic resonance fingerprinting (MRF) data for a region of interest in a subject using a MRI system, comparing the set of MRF data to an MRF dictionary to determine at least one parameter for the MRF data for the region of interest, generating a quantitative map of the at least one parameter, segmenting a target area of the region of interest based on the MRF data, generating at least one trajectory for placement of at least one electrode in the target area of the region of interest based on the segmentation of the target area and displaying the quantitative map and the at least one trajectory on a display.

17 Claims, 4 Drawing Sheets

(56) References Cited

OTHER PUBLICATIONS

Ma, D., et al. "Fast 3D magnetic resonance fingerprinting (MRF) for whole brain coverage in less than 3 minutes." Proceedings of the Annual Meeting and Exhibition of the International Society for Magnetic Resonance in Medicine, Singapore. 2016. (Year: 2016).*

Fernandes, Henrique M., et al. "Novel fingerprinting method characterises the necessary and sufficient structural connectivity from deep brain stimulation electrodes for a successful outcome." New Journal of Physics 17.1 (2015): 015001. (Year: 2015).*

Rieger, Benedikt, et al. "Time efficient whole-brain coverage with MR Fingerprinting using slice-interleaved echo-planar-imaging." Scientific reports 8.1 (2018): 1-12. (Year: 2018).*

Ma, D. et al., in "Magnetic Resonance Fingerprinting," Nature, 2013; 495 (7440): 187-192.

\* cited by examiner

SYSTEM AND METHOD FOR DEPLOYING INTERVENTIONAL MEDICAL DEVICES USING MAGNETIC RESONANCE FINGERPRINTING (MRF)

CROSS-REFERENCE TO RELATED APPLICATION

This application is based on, claims priority to, and incorporates herein by reference in its entirety U.S. Ser. No. 62/768,177 filed Nov. 16, 2018 and entitled "System and Method For Deploying Interventional Medical Devices Using Magnetic Resonance Fingerprinting (MRF)."

GOVERNMENT FUNDING STATEMENT

This invention was made with government support under EB016728, EB017219, NS105690, and NS085188 awarded by the National Institutes of Health. The government has certain rights in the invention.

BACKGROUND

Characterizing tissue species using nuclear magnetic resonance ("NMR") can include identifying different properties of a resonant species (e.g., T1 spin-lattice relaxation, T2 spin-spin relaxation, proton density). Other properties like tissue types and super-position of attributes can also be identified using NMR signals. These properties and others may be identified simultaneously using magnetic resonance fingerprinting ("MRF"), which is described, as one example, by D. Ma, et al., in "Magnetic Resonance Fingerprinting," Nature, 2013; 495 (7440): 187-192.

Conventional magnetic resonance imaging ("MRI") pulse sequences include repetitive similar preparation phases, waiting phases, and acquisition phases that serially produce signals from which images can be made. The preparation phase determines when a signal can be acquired and determines the properties of the acquired signal. For example, a first pulse sequence may produce a T1-weighted signal at a given echo time ("TE"), while a second pulse sequence may produce a T2-weighted signal at a different (or second) TE. These conventional pulse sequences typically provide qualitative results where data are acquired with various weighting or contrasts that highlight a particular parameter (e.g., T1 relaxation, T2 relaxation).

When magnetic resonance ("MR") images are generated, they may be viewed by a radiologist and/or surgeon who interprets the qualitative images for specific disease signatures. The radiologist may examine multiple image types (e.g., T1-weighted, T2 weighted) acquired in multiple imaging planes to make a diagnosis. The radiologist or other individual examining the qualitative images may need particular skill to be able to assess changes from session to session, from machine to machine, and from machine configuration to machine configuration.

Unlike conventional MRI, MRF employs a series of varied sequence blocks that simultaneously produce different signal evolutions in different resonant species (e.g., tissues) to which the radio frequency ("RF") is applied. The signals from different resonant tissues will, however, be different and can be distinguished using MRF. The different signals can be collected over a period of time to identify a signal evolution for the volume. Resonant species in the volume can then be characterized by comparing the signal evolution to known signal evolutions. Characterizing the resonant species may include identifying a material or tissue type, or may include identifying MR parameters associated with the resonant species. The "known" evolutions may be, for example, simulated evolutions calculated from physical principles and/or previously acquired evolutions. A large set of known evolutions may be stored in a dictionary. As mentioned, MRF permits simultaneous quantification of multiple tissue properties (e.g. T1 and T2).

Deep brain stimulation (DBS) is a neurosurgical therapy, analogous to cardiac pacemakers implanted in the brain, which is used to treat a wide range of neurological disorders, most notably Parkinson's disease (PD). For example, DBS has been used to control symptoms, such as rigidity, slowed movement, tremors, and walking difficulties in patients with Parkinson's. Other applications for DBS therapy include, for example, epilepsy, chronic pain, obsessive compulsive disorder, depression, etc.

DBS involves the implantation of an electrical stimulator into a defined area of a patient's brain, followed by delivery of high-frequency electrical impulses (e.g., up to 24 hours a day). Although the exact mechanism of action is not well understood, it is believed that electrical current produced by DBS interfere with or block brain activity close to the activation site. DB S therapies are intimately dependent upon accurate placement of the electrode(s) in the target brain region to achieve the desired therapeutic effects. However, most DBS targets are small nuclei in the brain, which are difficult to identify and visualize on a patient-specific basis using traditional MRI imaging. The most common surgical target for DBS is the subthalamic nucleus (STN) which is a structure with an approximate size of $10\times8\times5$ mm$^3$ that is not reliably visible on traditional MRI images. Other surgical targets for DBS include, for example, the vertralis internedius nucleus of the thalamus (VIM), the globus pallidus (GPi), etc. One common surgical targeting method uses preoperative MRI data and a brain atlas and attempts to fit the brain atlas to MRI images of the patient to estimate the location of a surgical target (e.g., STN). DBS surgical targeting methods that use a brain atlas, however, fail to account for patient to patient anatomical variability and inly provide an indirect estimate of the target in the patient's brain. Patient-to-patient variability in brain anatomy is substantial and the mechanical accuracy of stereotactic neurosurgical frame systems suffers from errors on the order of ~1 mm. As a result, about 15% of DBS leads are misplaced and require a revision surgery to correct their positioning. In addition, while DBS therapies are capable of generating good clinical responses, the technology has remained relatively limited in its clinical use. One major factor limiting the clinical growth of DBS is the lack of standardized and quantitatively validated methods for optimal patient-specific electrode placement. Such advances could enable a broader range of neurosurgeons (and hospital centers) to successfully deploy DBS therapies to their patients.

There is a need for a system and method to identify a DBS target (e.g., STN) on a patient-specific basis with a high degree of anatomical specificity and quantitative accuracy.

SUMMARY OF THE DISCLOSURE

In accordance with an embodiment, a method for target identification for a deep brain stimulation procedure includes acquiring a set of magnetic resonance fingerprinting (MRF) data for a region of interest in a subject using a MRI system, comparing the set of MRF data to an MRF dictionary to determine at least one parameter for the MRF data for the region of interest, generating a quantitative map of the at least one parameter, segmenting a target area of the region of interest based on the MRF data, generating at least one trajectory for placement of at least one electrode in the target area of the region of interest based on the segmentation of the target area and displaying the quantitative map and the at least one trajectory on a display.

In accordance with another embodiment, a system for target identification for a deep brain stimulation procedure, the system includes a stereotactic frame attached to a region of the subject and a magnetic resonance fingerprinting (MRF) system. The MRF system includes a magnet system configured to generate a polarizing magnetic field about at least a portion of a subject, a magnetic gradient system including a plurality of magnetic gradient coils configured to apply at least one magnetic gradient field to the polarizing magnetic field, a radio frequency (RF) system configured to apply an RF field to the subject and to receive magnetic resonance signals from the subject using a coil array; a computer system and a display. The computer system is programmed to acquire a set of magnetic resonance fingerprinting (MRF) data for a region of interest in a subject, compare the set of MRF data to an MRF dictionary to determine at least one parameter for the MRF data for the region of interest; generate a quantitative map of the at least one parameter, segment a target area of the region of interest based on the MRF data and generate at least one trajectory for placement of at least one electrode in the target area of the region of interest based on the segmentation of the target area. The display is configured for displaying the quantitative map and the at least one trajectory.

BRIEF DESCRIPTION OF THE DRAWINGS

The present invention will hereafter be described with reference to the accompanying drawings, wherein like reference numerals denote like elements.

DETAILED DESCRIPTION

Figure 1:
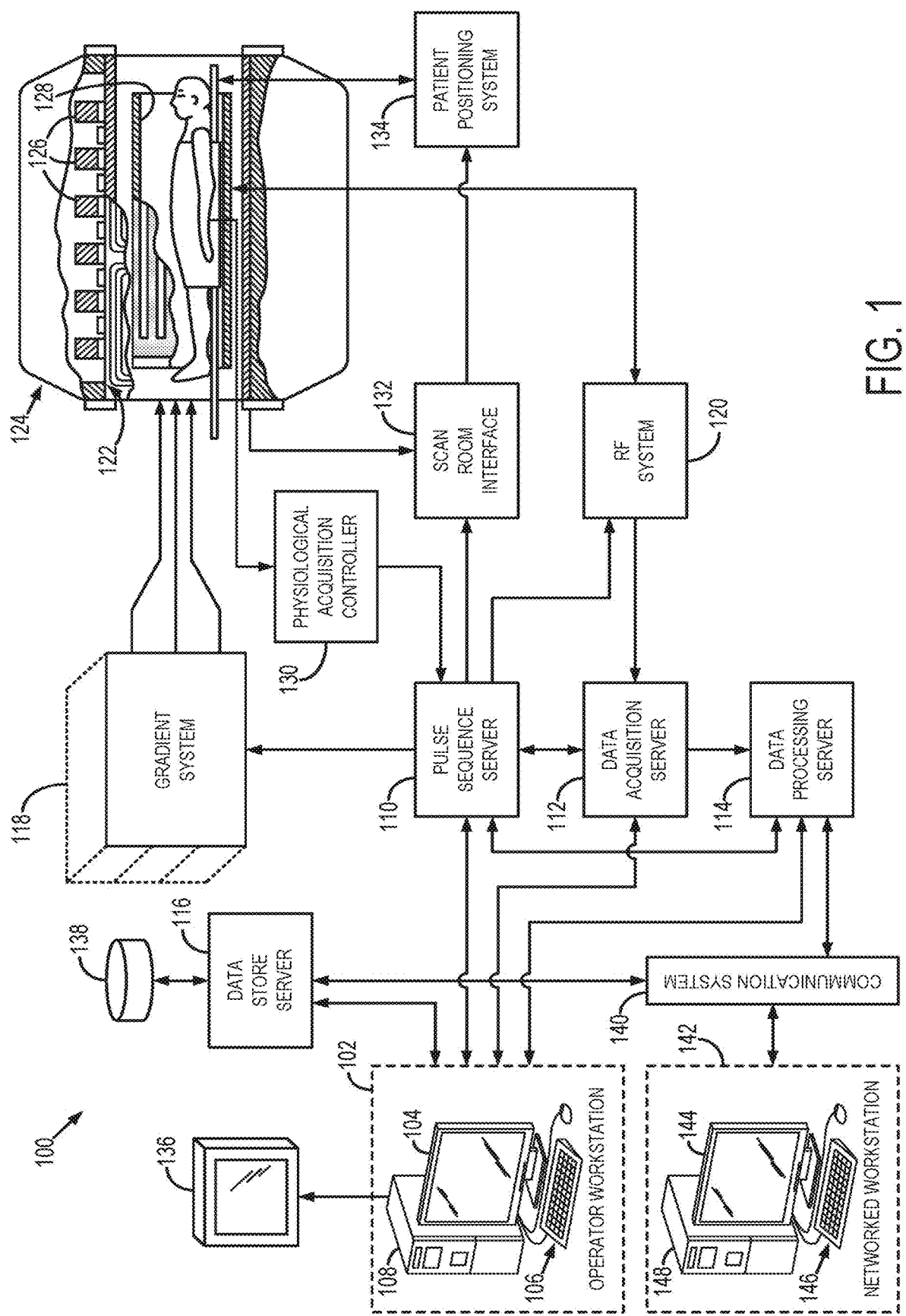
FIG. 1 is a schematic diagram of an example MRI system in accordance with an embodiment.

Magnetic resonance fingerprinting ("MRF") is a technique that facilitates mapping of tissue or other material properties based on random or pseudorandom measurements of the subject or object being imaged. In particular, MRF can be conceptualized as employing a series of varied "sequence blocks" that simultaneously produce different signal evolutions in different "resonant species" to which the RF is applied. The term "resonant species," as used herein, refers to a material, such as water, fat, bone, muscle, soft tissue, and the like, that can be made to resonate using NMR. By way of illustration, when radio frequency ("RF") energy is applied to a volume that has both bone and muscle tissue, then both the bone and muscle tissue will produce a nuclear magnetic resonance ("NMR") signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE'), and sampling patterns, such as by modifying one or more readout encoding gradients. The acquisition parameters are varied in a random manner, pseudorandom manner, or other manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, which as mentioned above may be random or pseudorandom, or may contain signals from different materials or tissues that are spatially incoherent, temporally incoherent, or both, MRF processes can be designed to map any of a wide variety of parameters. Examples of such parameters that can be mapped may include, but are not limited to, tissue parameters or properties such as longitudinal relaxation time ($T_1$), transverse relaxation time ($T_2$), and proton density ($\rho$) and device dependent parameters such as main or static magnetic field map ($B_0$). MRF is generally described in U.S. Pat. No. 8,723,518 and Published U.S. Patent Application No. 2015/0301141, each of which is incorporated herein by reference in its entirety.

The data acquired with MRF techniques are compared with a dictionary of signal models, or templates, that have been generated for different acquisition parameters from magnetic resonance signal models, such as Bloch equation-based physics simulations. This comparison allows estimation of the physical parameters, such as those mentioned above. As an example, the comparison of the acquired signals to a dictionary can be performed using any suitable matching or pattern recognition technique. The parameters for the tissue or other material in a given voxel are estimated to be the values that provide the best signal template matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative parameters, which can be extracted from the selected signal vector and used to generate the relevant quantitative parameter maps.

The stored signals and information derived from reference signal evolutions may be associated with a potentially very large data space. The data space for signal evolutions can be partially described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T_1, T_2, D) M_0; \quad (1)$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_i(\alpha)$ is a rotation due to off resonance; $R_{RF_{ij}}(\alpha,\phi)$ is a rotation due to RF differences; R(G) is a rotation due to a magnetic field gradient; $T_1$ is a longitudinal, or spin-lattice, relaxation time; $T_2$ is a transverse, or spin-spin, relaxation time; D is diffusion relaxation; $E_i(T_1,T_2,D)$ is a signal decay due to relaxation differences; and $M_0$ is the magnetization in the default or natural alignment to which spins align when placed in the main magnetic field.

While $E_i(T_1,T_2,D)$ is provided as an example, in different situations, the decay term, $E_i(T_1, T_2,D)$, may also include additional terms, $E_i(T_1,T_2, \ldots )$ or may include fewer terms, such as by not including the diffusion relaxation, as $E_i(T_1, T_2)$ or $E_i(T_1,T_2, \ldots )$. Also, the summation on "j" could be replace by a product on "j". The dictionary may store signals described by, $$S_i = R_i E_i(S_{i-1}) \qquad (2);$$

where $S_0$ is the default, or equilibrium, magnetization; $S_i$ is a vector that represents the different components of magnetization, $M_x$, $M_y$, and $M_z$ during the $i^{th}$ acquisition block; $R_j$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

Thus, in MRF, a unique signal timecourse is generated for each pixel. This timecourse evolves based on both physiological tissue properties such as T1 or T2 as well as acquisition parameters like flip angle (FA) and repetition time (TR). This signal timecourse can, thus, be referred to as a signal evolution and each pixel can be matched to an entry in the dictionary, which is a collection of possible signal evolutions or timecourses calculated using a range of possible tissue property values and knowledge of the quantum physics that govern the signal evolution. Upon matching the measured signal evolution/timecourse to a specific dictionary entry, the tissue properties corresponding to that dictionary entry can be identified. A fundamental criterion in MRF is that spatial incoherence be maintained to help separate signals that are mixed due to undersampling. In other words, signals from various locations should differ from each other, in order to be able to separate them when aliased.

To achieve this process, a magnetic resonance imaging (MRI) system or nuclear magnetic resonance (NMR) system may be utilized. FIG. 1 shows an example of an MRI system 100 in accordance with an embodiment. MRI system 100 may be used to implement the methods described herein. MRI system 100 includes an operator workstation 102, which may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \qquad (3);$$

and the phase of the received magnetic resonance signal may also be determined according to the following relationship:

$$\varphi = \tan^{-1}\left(\frac{Q}{I}\right). \qquad (4)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

The present disclosure describes a system and method that uses MRF for DBS surgical targeting to identify a target area of the brain (e.g., STN, VIM, and GPi) on a patient-specific basis. MRF provides improved anatomical specificity and quantitative accuracy for identifying the target area of the brain which allows accurate placement of electrodes in the target area of the brain. MRF may be used to provide a standardized image processing platform that simplifies DBS surgical targeting. MRF provides an improved dataset for DBS surgical targeting that may be acquired in less time than traditional MRI scan. In addition, MRF eliminates the need for use of a brain atlas to identify a DB S surgical target. MRF may be used to provide a quantitative standardization of MRI-based segmentation for patient-specific DBS target identification. MRF may be used to provide a reproducible and quantitative identification of a target areas, such as STN, and is directly measured from the patient.

Figure 2:
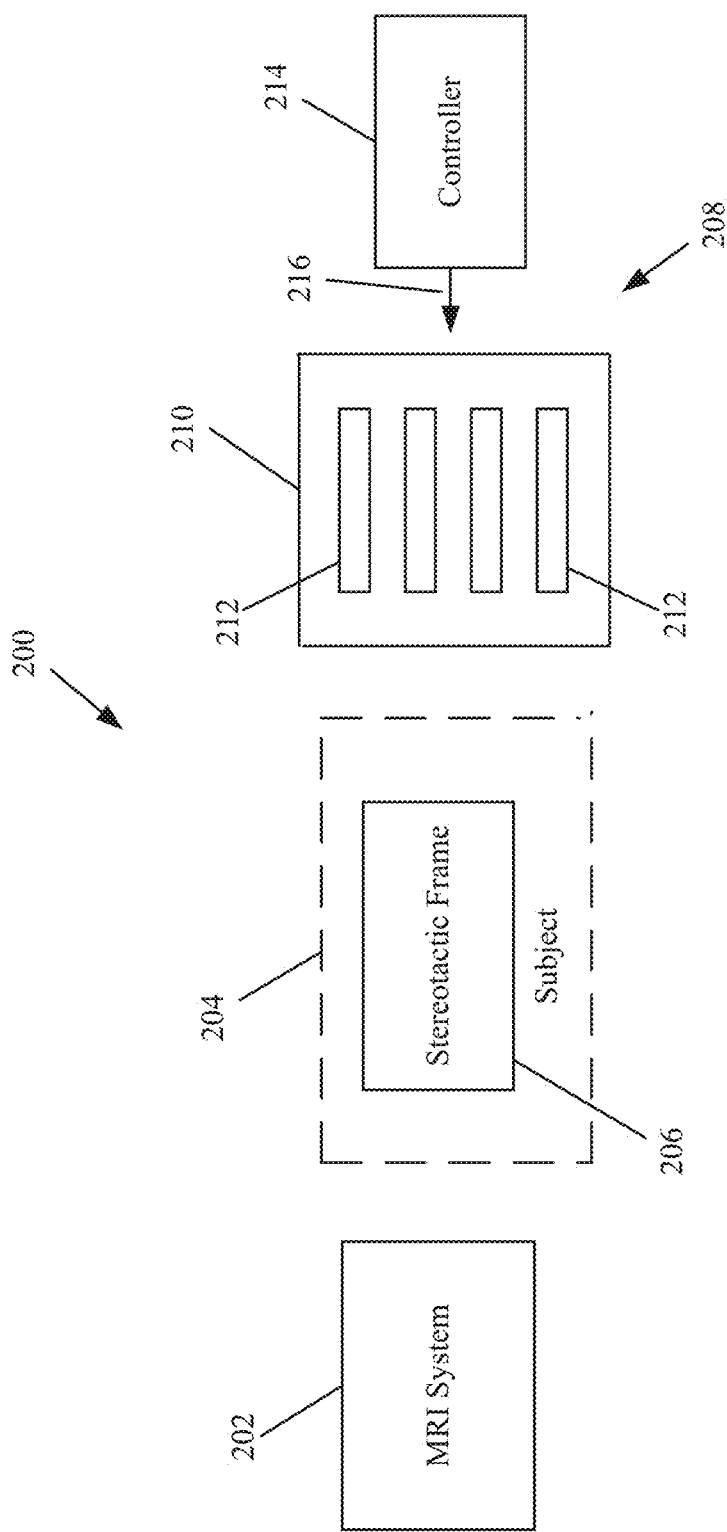
FIG. 2 is a block diagram of a system for identifying targets for deep brain stimulation (DBS) and positioning DBS electrodes in accordance with an embodiment.

FIG. 2 is a block diagram of a system for identifying target areas for deep brain stimulation (DBS) and positioning DBS electrodes in accordance with an embodiment. In FIG. 2, the system 200 includes an MRI system 202, a stereotactic neurosurgical frame 206 and a deep brain stimulation system 208. MRI system 202 may be a system such as, for example, MRI system 100 (shown in FIG. 1) that is configured to perform MRF acquisitions, imaging and mapping as described above. Stereotactic frame 206 is attached to a region of a subject 204, for example, for a DBS procedure the stereotactic frame is attached to a patient's head. The stereotactic frame 206 is used to provide a three dimensional coordinate system for spatialized localization in reference to a target image and may be used to determine coordinates of a target area within the region of interest. For a DBS procedure, the region of interest is the brain and the target area may be, for example, the subthalamic nucleus (STN), the vertralis internedius nucleus of the thalamus (VIM), the globus pallidus (GPi), etc. MRI system 202 may be used to acquire MRF data of a region of interest of the subject 204 and the stereotactic frame 206 as discussed further below with respect to FIG. 3. The MRF data may then be used to generate parameter maps and images that may be used in identifying and segmenting a target area (e.g., STN) of the region of interest (e.g., the brain) of the subject 204.

The identified target area may then be used to guide the placement of stimulators 212 of a deep brain stimulation system 208 in the region of interest (i.e., brain) of the subject 204. For example, the identified target area and coordinates relative to the stereotactic frame may be used to develop a surgical plan that includes, for example, trajectories for the placement of an electrode in the target area (e.g., STN) of the brain. Deep brain stimulation system 208 includes a stimulation assembly 210 and a controller 214. The stimulation assembly 210 may include a plurality of stimulators 212 configured to deliver stimulations to control brain activity in the subject 204. The stimulators 212 may include various electrodes or probes with electrical contacts configured for delivering electrical stimulations to the subject 204. In addition, the stimulation assembly 210 may also include various detectors or sensors capable of measuring brain activity in the subject 204. Stimulators 212 may be wholly or partially implanted in the target area of the brain of the subject 204. The controller 214 may be configured to perform a variety of functions for operating the stimulation assembly 210 such as, for example, sending and receiving instructions and operational parameters, the storage of operational or stimulation parameters and instructions to memory, and providing (e.g., with a signal generator) activating or command signals to the stimulators 212 to deliver electrical stimulations to various brain regions or tissues of the subject. Controller 214 may provide stimulation signals with various intensities, frequencies, phases, pulse widths, durations and waveforms. Controller 214 may include various connections, or terminals 118 for transmitting signals. The controller 214 may also be configured to detect brain signals acquired using the stimulation assembly 210. For example, the controller 214 may receive signals corresponding to brain activity in the one or more regions of the subject's brain.

Figure 3:
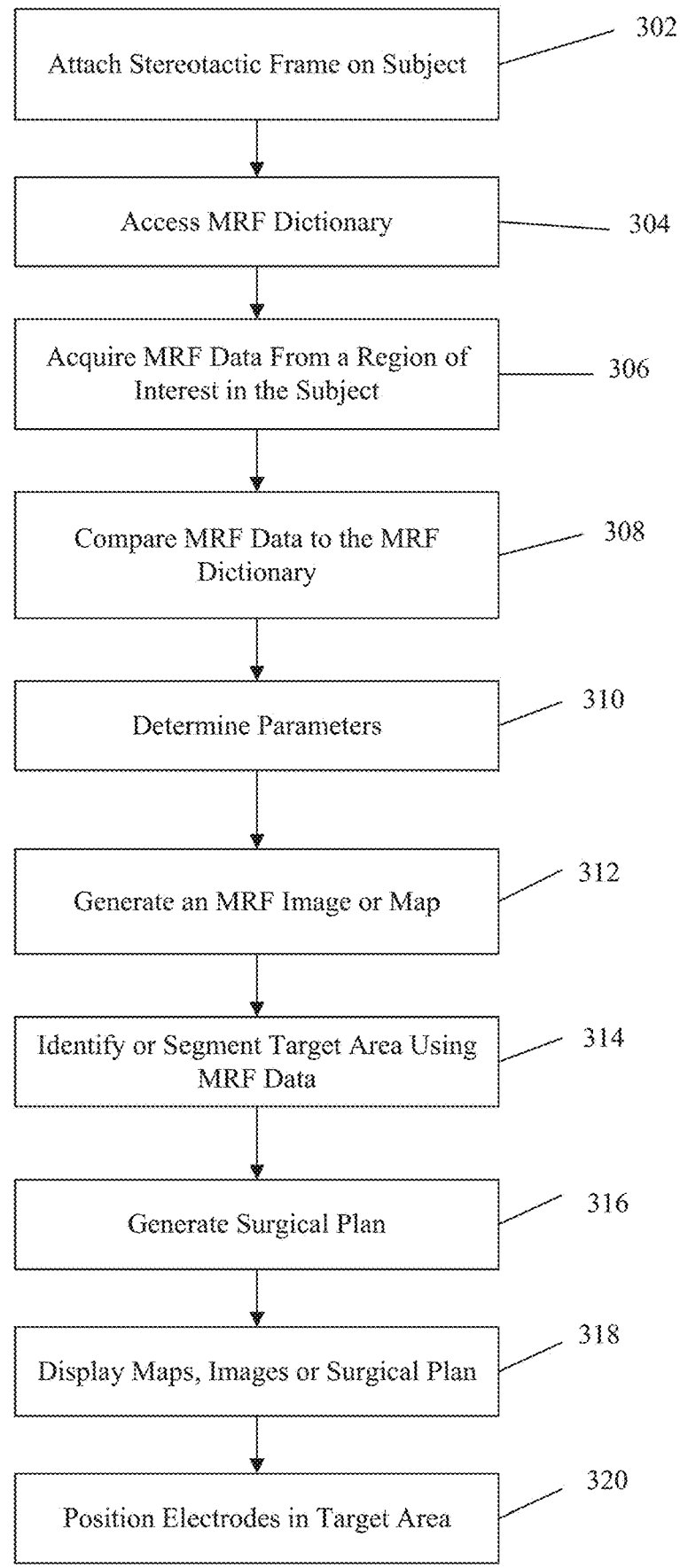
FIG. 3 illustrates a method for identifying targets for DBS and positioning DBS electrodes in accordance with an embodiment.

FIG. 3 illustrates a method for identifying target areas for DBS and positioning DBS electrodes in accordance with an embodiment. At block 302, a stereotactic frame (e.g., stereotactic frame 206 shown in FIG. 2) is attached to a region of a subject 204, for example, for a DBS procedure the stereotactic frame is attached to a patient's head. As discussed above, the stereotactic frame 206 is used to provide a three dimensional coordinate system for spatialized localization in reference to a target image and may be used to determine coordinates of a target area within the region of interest. As discussed above, for a DBS procedure the region of interest is the brain and the target area may be, for example, the subthalamic nucleus (STN), the vertralis internedius nucleus of the thalamus (VIM), the globus pallidus (GPi), etc. At block 304, an MRF dictionary is accessed. The MRF dictionary may be stored in memory or data storage of, for example, an MRI system (e.g., the MRI system 100 of FIG. 1) or other computer system. As used herein, the term "accessing" may refer to any number of activities related to generating, retrieving or processing the MRF dictionary using, for example, MRI system 100 (shown in FIG. 1), an external network, information repository, or combinations thereof. The MRF dictionary includes known signal evolutions (e.g., simulated signal evolutions). In an embodiment, the MRF dictionary may be generated using a Bloch simulation. At block 306, MRF data is acquired from tissue in a region of interest (e.g., the brain) in a subject using, for example, an MRI system (e.g., MRI system 100 shown in FIG. 1). Acquiring MRF data may include, for example, performing a pulse sequence using a series of varied sequence blocks to elicit a series of signal evolutions from a tissue in the region of interest. The MRF data may be acquired using a pulse sequence such as, for example, Fast Imaging with Steady-State Free Precession (FISP), FLASH, TrueFISP, gradient echo, spin echo, etc. The acquired MRF data may be stored in memory or data storage of, for example, an MRI system (e.g., the MRI system 100 of FIG. 1) or other computer system. In various embodiments, MRF data may be acquired before (i.e., preoperatively) a procedure to implant DBS electrodes in the brain of the subject, during (i.e., intraoperatively) the procedure or both before and during the procedure. As discussed further below, the MRF data acquired before and/or after the procedure is used to identify the target areas and guide the placement of electrodes.

The MRF data acquired at block 306 is stored and compared to the MRF dictionary at block 308 to match the acquired signal evolutions with signal evolutions stored in the MRF dictionary. Comparing the MRF data to the MRF dictionary may be performed in a number of ways such as, for example, using a pattern matching, template matching or other matching algorithm. In one embodiment, the inner products between the normalized measured time course of each pixel and all entries of the normalized dictionary are calculated, and the dictionary entry corresponding to the maximum value of the inner product is taken to represent the closest signal evolution to the acquired signal evolution. At block 310, one or more parameters of the MRF data are determined based on the comparison and matching at block 308. The parameters may include, for example, tissue parameters or properties such as longitudinal relaxation time (T1), transverse relaxation time (T2), and proton density ($\rho$) and device dependent parameters such as main or static magnetic field ($B_0$).

Figure 4:
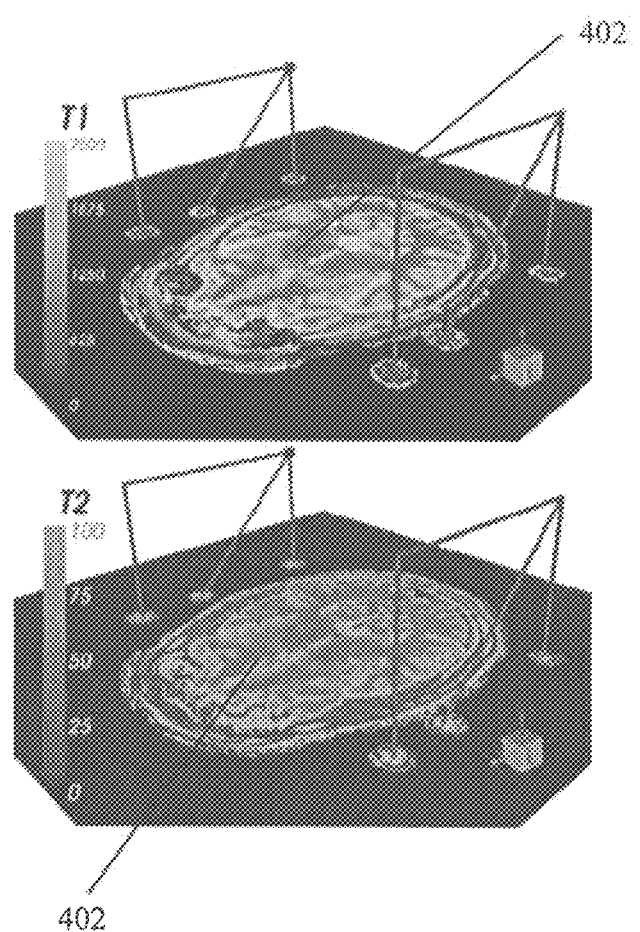
FIG. 4 shows an example whole brain MRF T1 and T2 maps acquired with a stereotactic neurological frame on a subject in accordance with an embodiment.

At block 312, images or maps may be generated indicating at least one of the identified parameters for the tissue in the region of interest in the subject. For example, a map may be generated having a quantitative indication of the at least one parameter. The images or maps may be provided and displayed on a display (e.g., display 104, 136 or 144 shown in FIG. 1). The images or maps may show markers from the stereotactic frame that may be used to determine coordinates of the target area (e.g., STN) of the region of interest in the subject. FIG. 4 shows an example whole brain MRF T1 and T2 maps acquired from a subject having an attached stereotactic neurological frame in accordance with an embodiment. FIG. 4 shows an example quantitative T1 map 402 and an example quantitative T2 map 404. In this example, the MRF data was acquired with a 3T MRI scanner and used to generate a fully quantitative 3D image of a while human brain with a MRI compatible stereotactic frame. The quantitative T1 402 and T2 404 maps were created at 1.2 mm isotropic resolution. Basic tissue clusters were calculated using k-means analysis and used to segment anatomical structures within the subthalamic region. In this example, the whole brain MF scan time was less than 12 minutes, including a B1 mapping scan to correct for inhomogeneity.

Returning to FIG. 3, at block 314, the target area of the region of interest is identified or segmented based on the MRF data. For example, the STN may be identified segmented using the acquired MRF data. In one embodiment, machine learning techniques may be used to identify the target region (e.g., the STN) in the MRF data. For example, a neural network may be trained using training MRF datasets for imaging of the brain such as, for example, for normal subjects and subjects with Parkinson's. In on embodiment, traditional brain atlas templates may be coupled to the MRF data to establish training information on the general location of the STN in the brain. The unique quantitative nature of the individual voxels may then be used to define the specific T1, T2, B0, etc. values that correspond to STN tissue. The MRF data acquired at block 306 or the images or parameter maps generated at block 312 may input to the trained neural network to identify the STN for the specific patient. In various embodiments, the separate trained neural networks may be created and customized for different subsets of patient, for example, for tissue characteristics of an old brain (i.e., >65 years old) or even more specifically for old PD brains. In another embodiment, the target region (e.g., STN) of the brain may be identified or segmented based on the MRF data using known segmentation techniques. In another embodiment, known segmentation techniques may be used to identify anatomical structures within the target region. For example, k-means analysis may be used to calculate basic tissue clusters that may be used to segment anatomical structures with the STN. In addition to identification or segmentation of the target area in the brain, coordinates of the target area of the brain may also be determined. As discussed above, markers from the stereotactic frame may be used to determine the coordinates of a target area within the region of interest.

At block 316, a plan (e.g., a trajectory) for positioning of the electrodes is generated based on the identified target region, coordinates and the generated maps or images. The surgical plan may include, for example, trajectories that indicate the depth an angle at which an electrode should be positioned in the target area of the brain. At block 320, the images, maps and surgical plans may be displayed on a display such as, for example, display 104, 136 or 144 shown in FIG. 1. At block 320, the electrodes may be positioned in the target area of the region of interest based on the surgical plan. The electrodes may be placed in the brain by, for example, a neurosurgeon performing the procedure. In one embodiment, the electrodes may be placed on both the left and right sides of the brain. The electrodes (e.g., stimulators 212 shown I FIG. 2) are placed in the target area of the brain through small holes made at the top of the skull of the patient. Typically, the electrodes are connected by long wires that travel under the skin and down the neck to a battery-powered stimulator (e.g., controller 214 shown in FIG. 2) positioned under the skin of the chest.

Computer-executable instructions for identifying target areas for deep brain stimulation and positioning deep brain stimulation electrodes according to the above-described methods may be stored on a form of computer readable media. Computer readable media includes volatile and non-volatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly states, are possible and within the scope of the invention. The order and sequence of any process or method steps may be varied or re-sequenced according to alternative embodiments.

The invention claimed is:

1. A method for target identification for a deep brain stimulation procedure, the method comprising:
    acquiring a set of magnetic resonance fingerprinting (MRF) data for a region of interest in a subject using a MRI system;
    comparing the set of MRF data to an MRF dictionary to determine at least one parameter for the MRF data for the region of interest;
    generating a quantitative map of the at least one parameter;
    segmenting a target area of the region of interest based on the MRF data;
    generating at least one trajectory for placement of at least one electrode in the target area of the region of interest based on the segmentation of the target area; and
    displaying the quantitative map and the at least one trajectory on a display.

2. The method according to claim 1, further comprising positioning at least one electrode in the target area based on the at least one trajectory.

3. The method according to claim 1, wherein the region of interest is the brain and the target area is the subthalamic nucleus (STN).

4. The method according to claim 1, wherein generating at least one trajectory for placement of at least one electrode in the target area includes determining a set of coordinates for the target area based on a set of markers from a stereotactic frame attached to the subject.

5. The method according to claim 1, wherein segmenting a target area of the region of interest include using a trained neural network to segment the target area.

6. The method according to claim 1, wherein the region of interest is the brain and the target area is the vertralis internedius nucleus of the thalamus (VIM).

7. The method according to claim 1, wherein the region of interest is the brain and the target area is the globus pallidus (GPi).

8. The method according to claim 1, wherein the at least one parameter is T1.

9. The method according to claim 1, wherein the at least one parameter is T2.

10. The system according to claim 1, wherein the computer system is further programmed to generating determine a set of coordinates for the target area based on a set of markers from the stereotactic frame attached to the subject.

11. A system for target identification for a deep brain stimulation procedure, the system comprising:
    a stereotactic frame attached to a region of the subject;
    a magnetic resonance fingerprinting (MRF) system comprising:
        a magnet system configured to generate a polarizing magnetic field about at least a portion of a subject;
        a magnetic gradient system including a plurality of magnetic gradient coils configured to apply at least one magnetic gradient field to the polarizing magnetic field;
        a radio frequency (RF) system configured to apply an RF field to the subject and to receive magnetic resonance signals from the subject using a coil array; and
    a computer system programmed to:
        acquire a set of magnetic resonance fingerprinting (MRF) data for a region of interest in a subject;
        compare the set of MRF data to an MRF dictionary to determine at least one parameter for the MRF data for the region of interest;
        generate a quantitative map of the at least one parameter;
        segment a target area of the region of interest based on the MRF data; and
        generate at least one trajectory for placement of at least one electrode in the target area of the region of interest based on the segmentation of the target area; and
    a display for displaying the quantitative map and the at least one trajectory.

12. The system according to claim 11, wherein the region of interest is the brain and the target area is the subthalamic nucleus (STN).

13. The system according to claim 11, wherein the region of interest is the brain and the target area is the vertralis internedius nucleus of the thalamus (VIM).

14. The system according to claim 11, wherein the region of interest is the brain and the target area is the globus pallidus (GPi).

15. The system according to claim 11, wherein the computer system is further programmed to segment the target area of the region of interest using a trained neural network.

16. The system according to claim 11, wherein the at least one parameter is T1.

17. The system according to claim 11, wherein the at least one parameter is T1.

* * * * *

UNITED STATES PATENT AND TRADEMARK OFFICE
CERTIFICATE OF CORRECTION

PATENT NO. : 11,372,069 B2
APPLICATION NO. : 16/686828
DATED : June 28, 2022
INVENTOR(S) : Mark A. Griswold et al.

It is certified that error appears in the above-identified patent and that said Letters Patent is hereby corrected as shown below:

In the Specification

Column 5, Line 11, "$E_i(T_1, T_2, ...)$" should be --$E_i(T_1, T_2, D, ...)$--.

Signed and Sealed this
Twenty-fourth Day of September, 2024

Katherine Kelly Vidal
*Director of the United States Patent and Trademark Office*